United States Patent
Reimer et al.

[11] Patent Number: 6,061,086
[45] Date of Patent: May 9, 2000

[54] APPARATUS AND METHOD FOR AUTOMATED VISUAL INSPECTION OF OBJECTS

[75] Inventors: Ernest M. Reimer; Paul Hearn, both of St. John's; Ivi Hermanto, Mount Pearl, all of Canada

[73] Assignee: Canopular East Inc., St. John's, Canada

[21] Appl. No.: 08/927,332

[22] Filed: Sep. 11, 1997

[51] Int. Cl.⁷ .............................. H04N 9/47; H06K 9/00
[52] U.S. Cl. .......................... 348/125; 348/89; 348/92; 382/141; 382/149
[58] Field of Search ................................ 382/148, 143, 382/149, 141; 348/86, 87, 88, 89, 92, 94, 95, 125, 128, 203, 204, 205, 206; 426/231

[56] References Cited

U.S. PATENT DOCUMENTS

| | | | |
|---|---|---|---|
| 3,704,342 | 11/1972 | Stoddard | 348/164 |
| 4,727,419 | 2/1988 | Yamada et al. | 358/101 |
| 4,744,131 | 5/1988 | Hartmann | 452/198 |
| 4,764,969 | 8/1988 | Ohtombe | 382/148 |
| 4,872,052 | 10/1989 | Liudzius et al. | 358/106 |
| 4,908,703 | 3/1990 | Jensen | 348/89 |
| 4,963,035 | 10/1990 | McCarthy et al. | 348/89 |
| 5,051,825 | 9/1991 | Cochran et al. | 358/106 |
| 5,255,114 | 10/1993 | Kessler | 359/196 |
| 5,257,101 | 10/1993 | Lee | 358/101 |
| 5,276,546 | 1/1994 | Palm et al. | 359/202 |
| 5,341,181 | 8/1994 | Godard | 351/210 |
| 5,444,480 | 8/1995 | Sumita | 348/127 |
| 5,473,931 | 12/1995 | Brady | 73/1.75 |
| 5,517,235 | 5/1996 | Wasserman | 348/126 |
| 5,608,563 | 3/1997 | Matsumura et al. | 359/202 |
| 5,784,484 | 7/1998 | Umezawa | 382/148 |
| 5,793,879 | 8/1998 | Benn et al. | 348/89 |

Primary Examiner—Vu Le
Attorney, Agent, or Firm—McFadden, Fincham

[57] ABSTRACT

The present invention relates to an apparatus and method for the automated inspection of objects for the presence of visual anomalies. The apparatus includes a first wide angle camera for acquiring an image of the object, a processor for detecting targets and generating target location from the image of the object, a two axis post-objective scanner associated with a high resolution camera for directing target image to the high resolution camera. The scanner provides a mechanism for saccadic emulation in combination with a high resolution video camera, which can be synchronized to the frame rate of the video camera for rapid high resolution examination of an object. The method according to the present invention comprises the steps of: capturing an image of at least a portion of an object; identifying visual anomalies as targets and detecting any targets on the object; generating location data for a detected target; emulating saccadic movement to selectively capture a high resolution image of a target; and generating an output for analysis. The apparatus and method are particularly suited for the automated detection of defects, in particular parasites, in fish fillets. It is an advantage of the present invention that post-objective scanning permits the camera to remain stationary, while only the mirrors are moved, to acquire high resolution data of substantially only the targets, resulting in increased speed and reduced processing time.

30 Claims, 5 Drawing Sheets

APPARATUS AND METHOD FOR AUTOMATED VISUAL INSPECTION OF OBJECTS

FIELD OF THE INVENTION

The present invention relates to a method and apparatus suitable for use in a machine vision automated inspection station. In particular the present invention relates to a method and apparatus for rapidly detecting and inspecting visual anomalies in objects.

BACKGROUND OF THE INVENTION

Machine vision has successfully been integrated into many manufacturing systems for automated inspection and automated control. Video cameras capture images with adequate resolution, typically 512×512. The image data can be stored and processed by a computer. With a narrow field of view, the resolution is sufficient for examining small details or detecting flaws for quality control. However, inspection of large areas at high resolution requires handling a very large volume of data. The penalty for detailed automated inspection is the time necessary for image acquisition and for analysis of the data. Many automated inspection applications have not been economically feasible due to time constraints and computing costs.

Automated inspection at high resolution is quite common. However, systems proposed are too slow to examine large areas or numerous sites effectively. For example, U.S. Pat. No. 5,517,235 issued to Wasserman, uses video cameras with zoom lenses to vary the field of view for inspecting printed circuit boards. A smaller field of view, and hence higher resolution, is needed to examine boards or parts of boards with greater density of components. The inspection head is advanced across a viewing table to acquire a complete image. Multiple passes may be made to increase the resolution for examining critical areas flagged in the initial inspection. Physical movement of the head back and forth, and zoom lens control are relatively slow and not selective for examining specific locations. Even if only a small field of high resolution data is to be acquired, the head must pass over the complete object to locate the area.

Closer examination of specific sites of interest is also proposed as in U.S. Pat. No. 5,051,825 issued to Cochran and Austin, which uses a first video camera to determine the position and orientation of the article using geometrical determination, and a second video camera which simultaneously captures an image of higher resolution while the article is advanced across the field of view. This is a slow process. Acquiring a full image at high resolution presents greater time and system capability demands.

U.S. Pat. No. 4,872,052 issued to Liudzius, et al., discloses a system for examining semi-conductors which assembles images from multiple angles of view for examining a three-dimensional object at low resolution. The system also includes a high resolution camera which receives location information from the low resolution image to adjust the image registration to the standard comparison data. The high resolution camera is moveable on an X-Y plane parallel to that of the semi-conductor in order to acquire target image data. It is provided with a focus compensating device for fine adjustment to the high magnification without changing the focal length. Moving the camera across the object and further manipulating a focus compensating device are both complicated mechanically and slow. It is not anticipated by this prior art design to examine numerous targets at high resolution.

Slow mechanical positioning or acquisition of large volumes of unnecessary data have rendered prior art automated inspection systems too slow to be appropriate for high resolution examination of numerous sites, or for relatively high speed automated processing.

Scanners for precise and rapid positioning of optic mirrors have been used for raster scanning to acquire detailed composite information, such as in confocal microscopes, CAT SCAN and MRI medical imaging equipment, and in industry for example in three dimensional imaging techniques. The raster scan makes a complete pass across the object assembling data line by line. A more complex scanner system includes two axes of rotation, offering precise positioning to any point across a plane within angular limitations. Dual axis scanners have been used for directing lasers, for instance in targeting systems, and light show demonstrations. A dual axis scanner generally combines a high quality optic mirror mounted on a magnetically driven armature with a position detector and a digital driver. The accuracy of dual axis scanners can be within a few microradians.

Use of a two axis scanner is proposed in U.S. Pat. No. 5,608,563 issued to Matsumura et al. in order to rapidly position a scanner to lines which contain data only. The scanner is used in cooperation with a projection apparatus rather than for data acquisition. Time is saved by not scanning lines which do not contain data. However, the location of lines containing data is known in advance and stored in the system before scanning begins. The system cannot be used to locate previously unknown targets.

In the inspection of regular objects a comparison to a reference standard or template is easily made. Regular objects are well suited for geometrical analysis and standard comparison. Once position registration is established, target location information can be pre-programmed. The elements of interest have known configurations and positions, reducing processing time and scanning requirements.

Objects, such as food and textile products in particular, can be highly variable in shape and texture and pose a significantly more difficult problem for machine vision inspection. In some cases parameters can be prescribed, or statistical analysis can predict reliable results. Foreign objects, however, defy any classification of this kind. Foreign objects may have unpredictable size, shape, material, position, orientation, and number which require a more adaptable approach to automated detection and analysis leading to identification. The more complex processing and resultant time required make rapid detection and acquisition of targets image data more important for achieving an efficient system.

In both cases the rapid detection of targets, acquisition of data and reduced processing time are important in producing an effective automated system.

Human visual inspection is commonly used for quality control for rapidly identifying superficial imperfections or blemishes. The eye is quickly drawn to irregularities from a broad scan of the object. The response is referred to as an attention mechanism. Features, such as motion and contrast, primarily detected by human vision, are of interest to quantify in order to emulate the attention mechanism in automated systems. Other features such as color, texture and alignment can be used similarly by automated systems.

The present invention was developed for the inspection of fish fillets for defects, primarily parasites. This is an area which has been difficult to automate. Most production functions in fin fish processing have been fully automated, but defect inspection still requires skilled quality inspection personnel. Surface and near surface parasites are currently detected by human visual examination on a candling table which provides back lighting through the fish fillet and highlights characteristic shadows that correspond to parasites. This is, obviously, a labor-intensive operation which adds to the production costs.

This application presents significant additional challenges to automated inspection. The fillets do not have a regular shape or size. Objects of interest must be located and distinguished from other visual features such as blood spots, traces of skin or strands of stomach lining which often have quite similar characteristics. Unlike other industrial inspection applications, the parasites do not have a fixed shape, size or number and are often transparent offering very low contrast. To make determinations of this kind, relatively high resolution is required which can match human capabilities. To be commercially useful, analysis must occur in a relatively short time scale. Human analysis requires approximately 3 seconds per side of each fillet. An automated system with a throughput of one fillet per second is desirable for economic substitution.

The limitation to providing high resolution imaging at human equivalent or even closer detail is the shear volume of data such an operation would create. A high resolution image of a whole fillet would be too large for processing and analysis in a useful time scale. A fillet of an estimated 200 mm×400 mm, at human equivalent resolution of 5 lines per mm, would generate an array of approximately 3000×6000 pixels. The sensors necessary to pick up such a large array are very expensive. A system capable of capturing and processing data at the necessary rate cannot be economically implemented. Emulation of human eye performance cannot be achieved using brute force.

To achieve human equivalent resolution, it has been proposed in the present invention to mimic human visual processing. The human eye has a small central color sensitive area made up of cones capable of very high resolution. The majority of visual sensors which comprise the peripheral vision system are lower resolution monochrome rods. In human visual inspection, a broad scan by the peripheral vision system uses the attention mechanism to provide an initial identification of anomalies. The central vision system is then used to examine anomalies in detail for final identification. Eye movement, known as saccadic fixation, jumps to relocate the eye position approximately 3–10 times per second having the effect of assembling a composite view of successive high resolution images. Imitating this two stage vision hierarchy involves collection of low resolution scene information over a wide area (typically 0.6 radian solid angle), providing an attention mechanism and directing a narrow field of view (about 17 mrads at a resolution of about 0.1 mrad) for close inspection of features of interest to assemble substantially complete high resolution information. Human eye saccadic fixation rate at about 10 Hz has been emulated in a camera orienting system known as Agile Eye™. However, the selective acquisition of high resolution information at relatively high speed (30–60 Hz) has not previously been achieved.

The present invention utilizing the post-objective scanning design to provide saccadic emulation, imitates human visual acquisition at an order of magnitude faster. By achieving a 30–60 Hz acquisition rate, data acquisition can be matched to the normal frame rate of a video camera, as commonly available, to capture 30 frames or 60 fields per second. Thus a relatively simple and inexpensive system is optimized to view an entirely different scene with each frame or field.

SUMMARY OF THE INVENTION

The present invention has found that significant savings in time can be achieved using the rapid and precise positioning capability of a two axis post-objective scanner in cooperation with a visual image sensor. Physical positioning time is reduced, and only selected high resolution data is acquired for processing. A video camera with a narrow field of view can be directed selectively to acquire only necessary target data, without acquiring high resolution image data of the complete object or scanning past the complete object thus reducing the total volume of data which must be handled. Preferably, the system according to the present invention is used in combination with an additional video camera having a wide field of view and an initial attention mechanism, such as blob analysis or other known image processing routines, to generate locations for closer inspection by the high resolution system.

Accordingly, the present invention provides an apparatus for the inspection of objects in an inspection field for the presence of a target, comprising:

a light source;

first processor means for detecting a target and for generating location data for a target;

optic sensor means for selectively acquiring high resolution image data of a located target;

positioning means for saccadic emulation associated with the optic sensor means for directing the image data from a target location to the sensor; and second processor means for generating an output from the target image data for analysis.

In a preferred embodiment, the present invention further includes a wide angle optic sensor means to acquire image data of the object to provide to the first processor means for detecting any target and for generating location data for each target.

In a preferred embodiment, the present invention further includes a high resolution optic sensor means having a smaller field of view than that of the wide angle sensor means, wherein the high resolution image includes a target substantially in the absence of unnecessary data.

In a further embodiment, the present invention provides an apparatus for the inspection of objects for the presence of targets including an optic sensor, the improvement comprising positioning means for saccadic emulation associated with the optic sensor for directing image data of a target to the sensor including a post-objective scanner.

In an additional embodiment, the present invention comprises an apparatus for the inspection of objects for visual targets, comprising:

a light source;

a first video imaging means for acquiring a visual image having a field of view including at least a portion of an object and for transmitting image data to a central processor;

a second video imaging means for acquiring a second visual image having a field of view smaller than the field of view of the first video imaging means and for transmitting image data to a central processor;

a central processor for receiving image data from the first and second video imaging means and for generating an output for analysis including:

a frame grabber for converting the image data of first and second video imaging means to digital data and isolating a single image;

a digital signal processor assembly programmed for morphological manipulation of the image data from the first video imaging means to detect individual visual anomalies as targets and for generating location coordinates for each target; and a post-objective scanner associated with the second video imaging means including:

a mirror directable in two axes for selectively directing image data from a specified target location to the second video imaging means, and a driver for accessing location coordinates and directing the mirror towards a target location.

A particular embodiment of the present invention comprises an automated station for the detection of defects including parasites in fish fillets, including:

a viewing head comprising:

first image recording means for acquiring image data of an object in an inspection field;

second image recording means having a smaller field of view than that of the first image recording means for selectively acquiring higher resolution image data;

positioning means associated with the second image recording means, for directing image data of substantially only a target to the second image recording means including a post-objective scanner directable in two axes toward any location on a plane in the inspection field;

a candling table for back-lighting a fillet;

a light source for providing illumination of the inspection field;

advancing means for presenting a fillet on the candling table to the first and second cameras;

a support for supporting the viewing head a distance from the candling table;

first processor means for processing the image data of the object to isolate any targets, and for generating location data for each target; and second processor means for generating an output from the target image data for analysis.

A preferred method, according to the present invention, for the inspection of objects for the presence of targets comprises:

detecting any targets on the object;

generating location data for a detected target;

emulating saccadic movement to selectively capture a high resolution image of a target; and generating an output for analysis.

Preferably, the method according to the present invention further includes synchronizing the saccadic movement emulation to sequentially capture a high resolution image of each target detected at the frame rate of a video imaging means.

A further preferred method according to the present invention comprises a method for the inspection of fish fillets for the presence of defects including parasites, comprising the steps of:

capturing an image of at least a portion of a fillet;

detecting any defects or potential parasites as targets;

generating a location for a detected target;

emulating saccadic movement to selectively capture a higher resolution image of a target;

processing target image data to determine whether a target is a defect or parasite; and identifying a fillet having a defect or parasite.

It is an advantage of the present invention to provide the capability to detect targets, and to be able to selectively isolate targets for detailed examination. Speed is gained according to the present invention by acquiring only necessary high resolution data for processing and analysis. The system advantageously reduces the amount of data to be processed and consequently the time required. Post objective scanning permits the camera to remain stationary as only the mirrors need to be moved. As a result, the speed is increased to accurately enable image acquisition synchronous with the frame rate of a standard video camera, and the driving power is reduced.

It is a further advantage to achieve fast and accurate performance utilizing commonly available, and hence cost effective, hardware.

The present invention is suitable for many visual examination tasks, particularly where multiple target acquisition is necessary, or in the examination of a relatively large field in a short time period. This system can be adapted for use in other examination tasks where identification in complex and irregular scenes must be made, such as other areas of food processing, inspection of natural materials, and medical diagnostics.

BRIEF DESCRIPTION OF THE FIGURES

The invention will be readily understood by the following description of a preferred embodiment with reference to the following drawings in which.

Like numerals are used throughout to designate like elements.

DETAILED DESCRIPTION OF THE PREFERRED EMBODIMENTS

Figure 1:
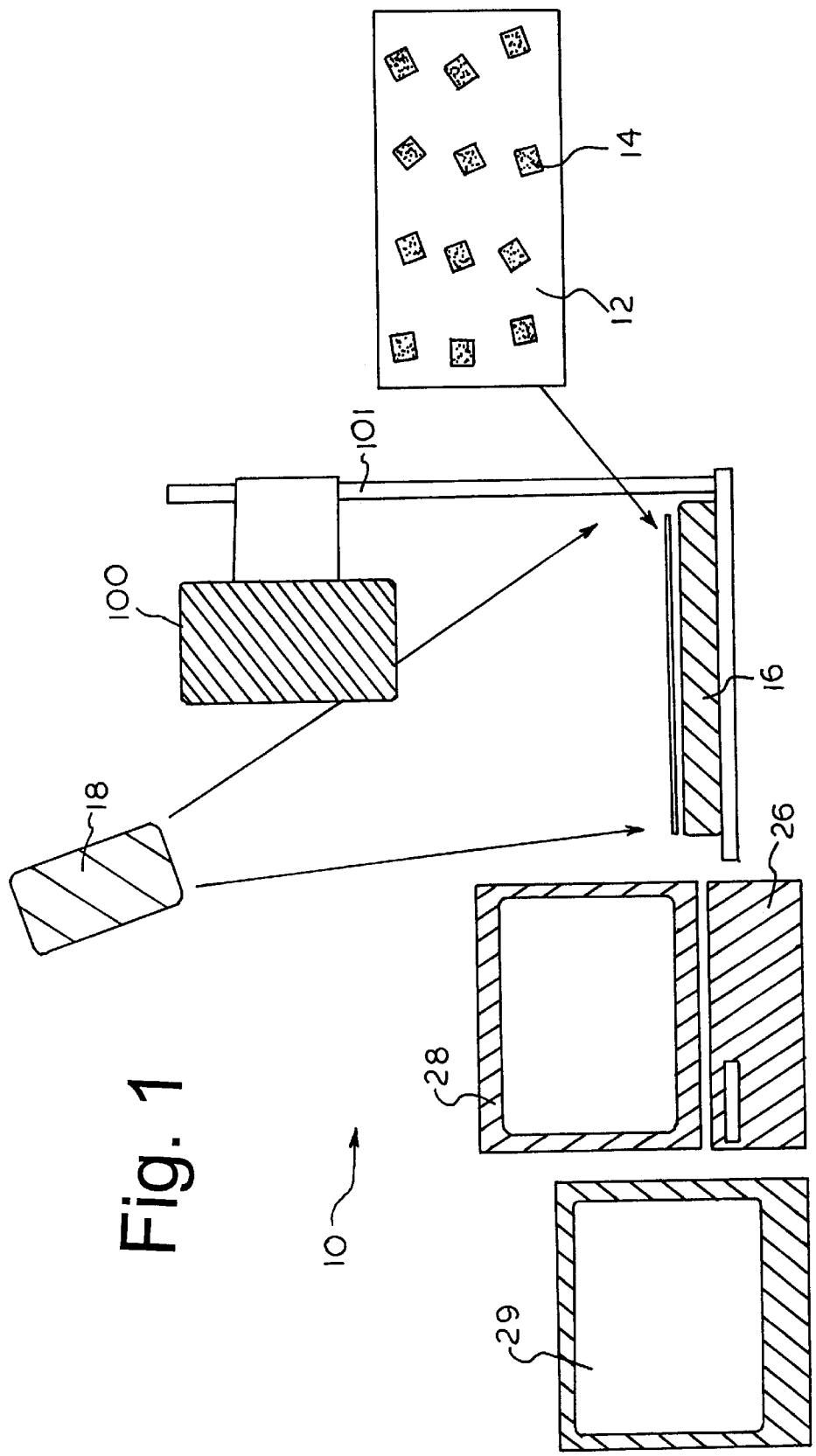
FIG. 1 is a schematic illustration of a bench scale embodiment of the present invention.

An embodiment of the invention as a system is shown generally as 10 in FIG. 1. As seen in a schematic bench scale model, a scan head 100 is adjustably mounted on a standard 101. The object 12 having test targets 14 is presented to the cameras 20, 30 in the scan head 100, on table 16. The cameras 20, 30 are preferably video imaging means, such as CCD (charge coupled device) video cameras. Other equivalent image recording means may be substituted. A candling table 16 is provided for back-lighting a fillet 12 in the case of fish inspection. The image data acquired by the cameras can be displayed on the monitor 28, or in real time on the video monitor 29. General lighting 18 is also provided. Lighting requirements, as known in the art, will change for each application. In this configuration the object 12 is presented manually and remains in the same position for image acquisition by the low and high resolution cameras 20, 30. The system 10 can also operate in a dynamic mode (seen in FIG. 3) with the objects 12 travelling on an continuous motion conveyor 116 at a fixed rate.

Figure 3:
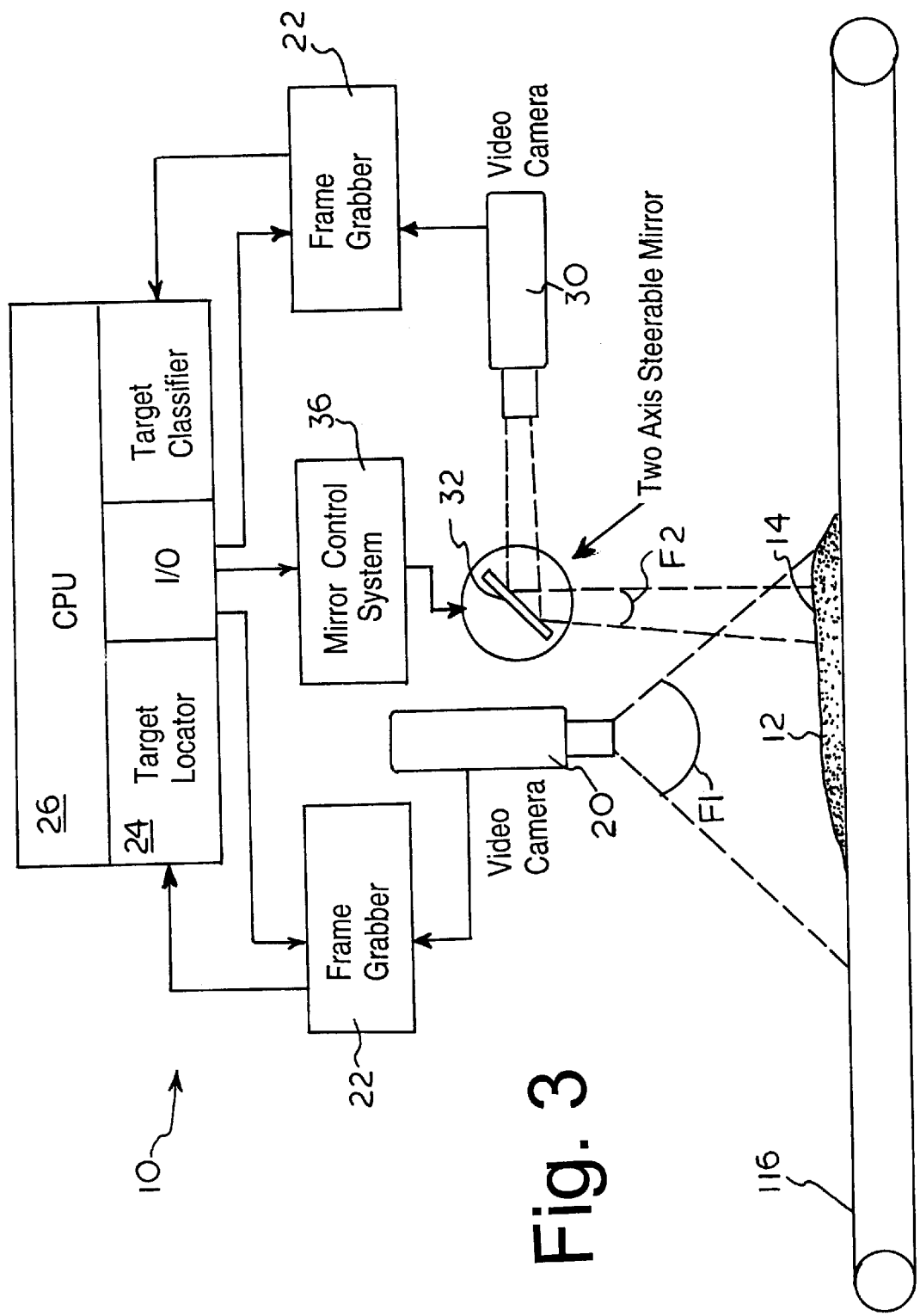
FIG. 3 is a schematic illustration of the embodiment of FIG. 1 showing the logical process path.

As represented in FIG. 3, the first camera 20 has a wide field of view $F^1$ which includes the entire object 12. A second camera 30 with a high magnification lens 31 has a narrow field of view $F^2$ including only a reduced portion of the object 12 large enough to capture a potential target 14 at higher resolution substantially in the absence of unnecessary data. The narrow field of view $F^2$ can be adjusted to accommodate the anticipated target size. If the speed of operation is reduced, the field of view $F^2$ can be variable, for instance using an automatic zoom lens, in response to the actual target size 14. Similarly, under reduced speed operation, a single camera can be adapted to work in low resolution and high resolution modes using an automatic zoom lens to change the field of view.

Figure 2:
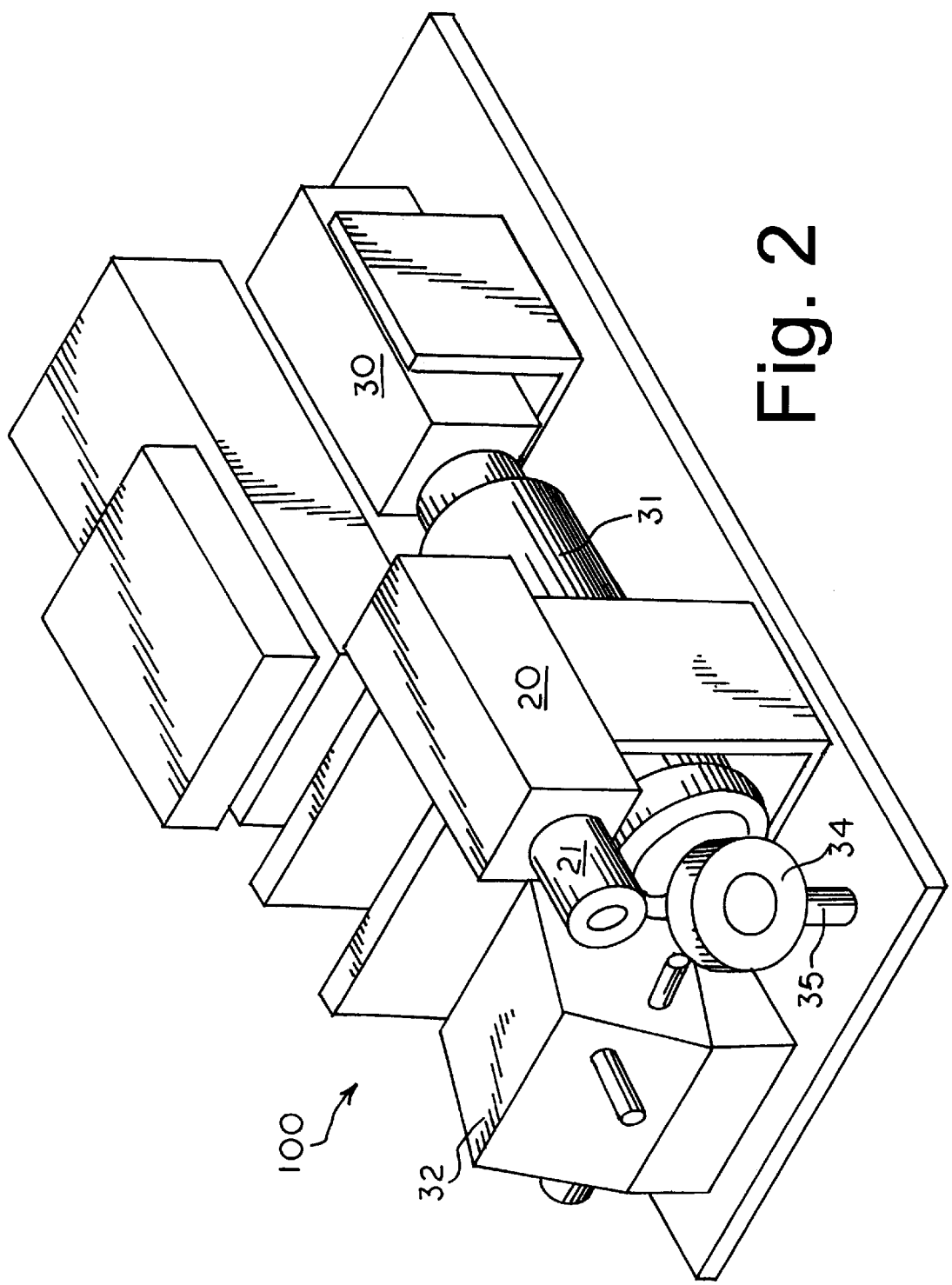
FIG. 2 is a cut-away view of the scan head of FIG. 1.

A positioning device 32 comprises a high speed two-axis post-objective optical scanner for directing the field of view of the second camera 30. Seen in detail in FIG. 2, the scan head 100 houses a first low resolution camera 20 and lens 21, and a high resolution camera 30 which cooperates with a high magnification lens 31, an x-y scanner 32 having a mirror 34 on a mount 35 for two axis rotation.

Associated with the first CCD camera 20 for processing controlled by a CPU 26, seen schematically in FIG. 3, is a frame grabber 22 for isolating a single digital image and a target locator 24 for detecting visual targets and for generating x-y coordinate target location information. Coordinate location information is provided to a scanner driver 36 for directing the field of view $F^2$ of the second camera 30 towards a target. At 30–60 Hz the scanner 32 directs new image data isolated by the frame grabber 22 at the frame rate of the camera 30. The CPU 26 also provides synchronization for the lighting 16, 18, cameras 20, 30, and scanner 32. Processing operations associated with each camera are shown as separate loops, however the necessary hardware is actually common between them.

Processing in the CPU 26 generates target location data, depending on the application, from a data table in combination with position registration information from a first sensor, a subtraction operation, location or image information from a first sensor. The first sensor is provided to identify the presence of an object and the location of targets. Since the initial identification is not for visual analysis, other sensors, as available in the art, may be used to generate location information. Targets maybe pre-marked for detection with appropriate detection means, for instance by florescence in combination with a photodetector, or other well known markers. Advantageously target locations are identified from a first low resolution image acquired by a visual sensor, such as a line scan or CCD camera, for the inspection of irregular objects with a blob analysis routine, or comparable pattern recognition operation to detect targets and generate locations for detailed inspection. A frame grabber system 22 is required which can perform image digitization and image processing within one second. A programmable DSP (digital signal processor) board or board with multiple DSPs 24, for blob analysis or other known image processing routines, may be interfaced with the frame grabber 22, for instance, to achieve the processing speed required to detect targets.

A second CCD camera 30 and high magnification lens 31 acquire isolated target image data, without unnecessary high resolution data. The scan system 32, 34, 36, allows the high resolution camera 30 to selectively obtain visual data from any location on the surface of the fillet 12 without taking a high resolution image of the whole object 12. The scanner 32 has a mirror 34 with two axis control at very rapid access time to direct light back to the high resolution camera 30. The scanner 32 and mirror 34 effectively position the field of view of the high resolution camera 30 anywhere in the object field.

In operation the first camera 20 acquires a low resolution image which is processed only once per object 12 to detect any targets 14. A frame grabber 22 isolates a single frame and converts the visual data to digital data. Processing in the central processor 26 using a blob analysis routine or equivalent target locator 24 then generates coordinates indicating the location of the targets 14. Coordinate data is used to drive the scanner 32, and mirror 34 sequentially to each location where the second camera 30 obtains high resolution image data of each target 14 within a narrow field of view. The high resolution target image data can then be processed for further analysis, such as a running count, comparison, categorizing, acceptance or rejection, etc. The presence of known features may be subtracted leaving only foreign anomalies for inspection.

Visually targets are identified by shape, color, contrast, texture or other changes in appearance which may be highlighted by lighting techniques such as lighting angle or back lighting, selected colored light, edge detection, misalignment, surface irregularity, color value, as known in the art. Processing visual data to detect targets may be specified to certain parameters or compared to a data library using algorithmic morphological manipulation such as blob analysis, thresholding, edge detection, dilation, erosion, subtraction, inter alia known in the art, which will vary depending on the specific application. The benefit in more specific target detection is that fewer target images must be acquired and processed, thus increasing throughput speed.

Figure 5:
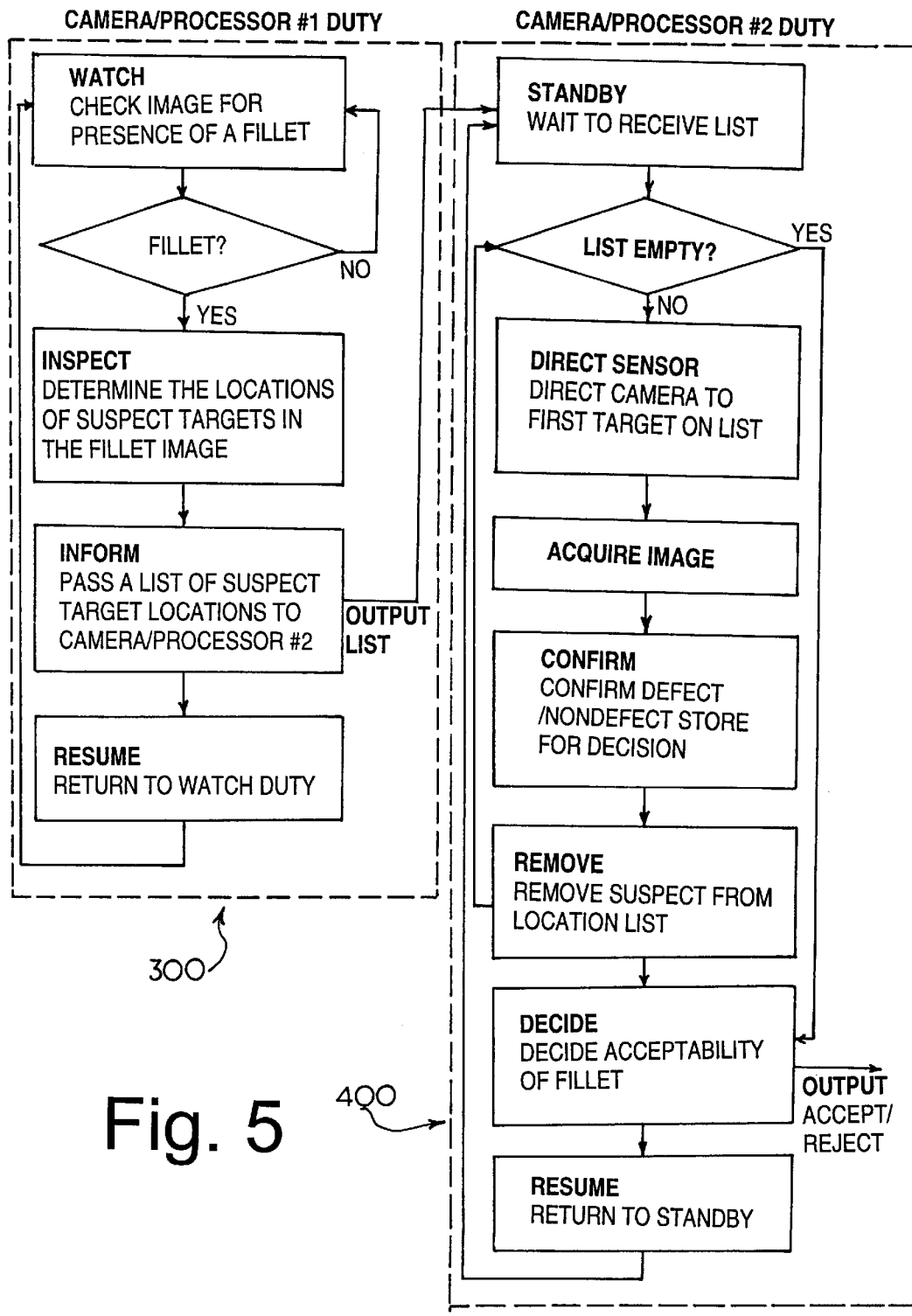
FIG. 5 is a flow chart schematically illustrating the first and second processor routines.

FIG. 5 illustrates the first processor routine 300, and the second processor routine 400 in a fillet inspection application. In this preferred operation, as seen in 400, each target is inspected sequentially. A final output is made to accept or reject the fillet. The system then returns to wait for the next fillet.

Figure 4:
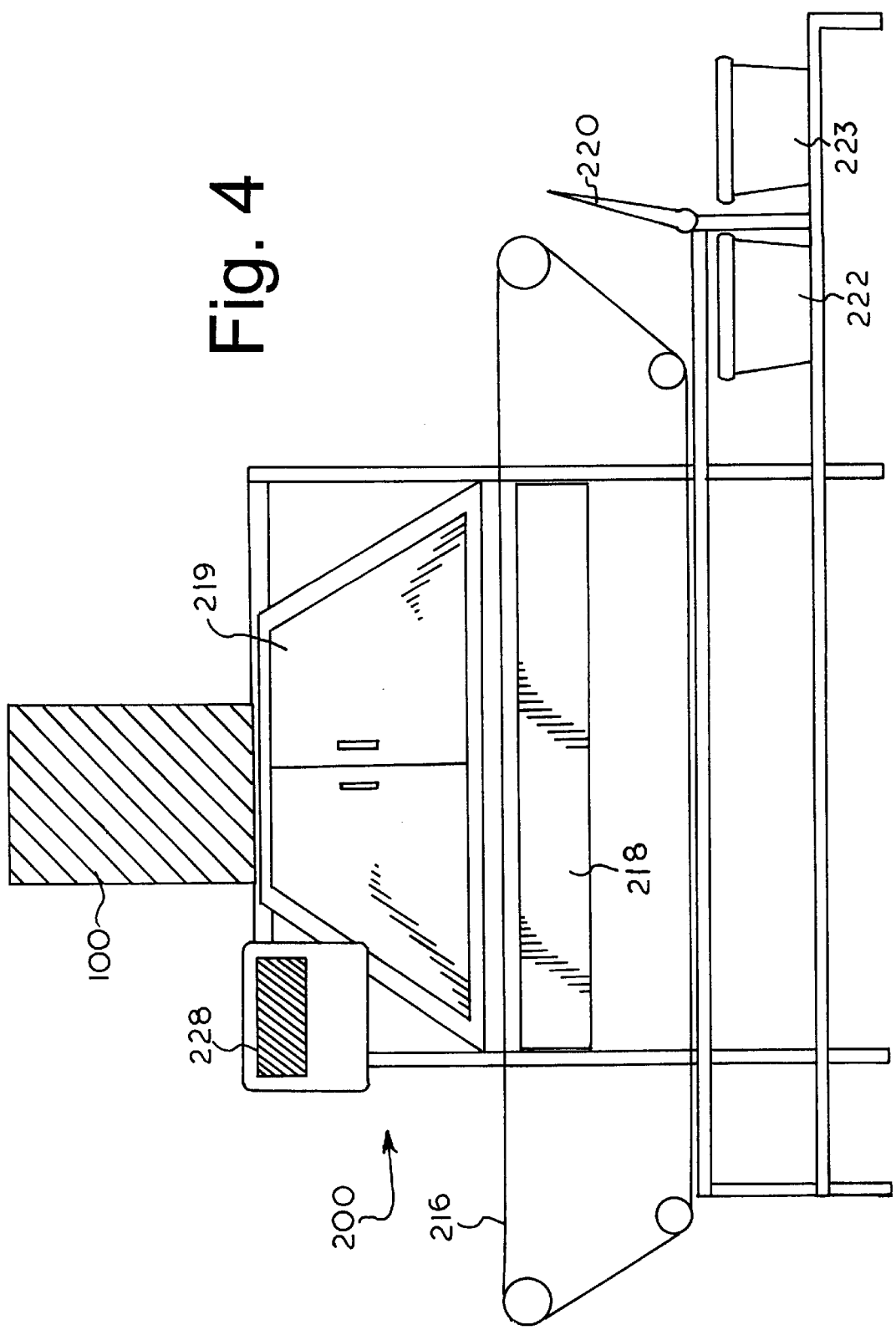
FIG. 4 is a schematic illustration of an embodiment of the present invention for the inspection of fish fillets.

As seen in FIG. 4 an embodiment including the present invention for fish inspection 200 includes a feed conveyor 216 adapted to stop at the inspection station or to advance the fillet 12 through at a controlled rate. Fillets 12 may be supplied from an additional conveyor upstream (not shown), or by manual placement. The inspection station comprises a candling light source 218, a scan head 100 (housed in a protective upper cabinet 219 shrouding the inspection field, and preferably separated by glass from the fish handling environment) and a computerized control interface 228. Once the inspection is complete the fillet 12 is advanced by the conveyor 216 and classified according to the results. This is represented by a mechanical deflector 220 and separate containers 222, 223. Separate outfeed conveyors (not shown) may alternatively be provided to convey the separated fillets for further processing according to the inspection results.

The scan head 100 for parasite detection uses two low resolution (eg. 512×512 pixel) CCD video cameras, preferably having 24 bit color capability. For the present application, the lowest acceptable resolution to detect all potential targets in the low resolution camera 20 is 550 $\mu$m or 0.5 lines per mm, for instance using a 6 mm lens. In this application a resolution of 78 $\mu$m or 5 lines per mm is needed for reliable discrimination of features using a 60–300 mm lens 31 with the high resolution camera 30. This provides a first field of view of approximately 200×400 mm and a narrow field of view of approximately 10–40 mm square. A scanner controllable over ±20° at 3 msec. access time is used in the present embodiment. The mirror 34 is 10 mm, selected to cooperate with the aperture of the high resolution camera 30. Intense illumination is provided to compensate for a relatively small mirror which reduces drive power requirements and increases positioning speed. In the fillet inspection application approximately 20–30 targets per fillet must be inspected at high resolution in the one second throughput time. The elements used in this application have been selected as commercially available components for cost control. As apparent to a person skilled in the art, equivalent components can be substituted for specific applications as needed.

The device according to the present invention has also been adapted for the identification of visual blemishes in other applications, such as paint and other surface treatments in manufactured articles. Changes in color, texture, contrast and shape are easily identified. For large articles a series of inspections may be needed to inspect the complete object.

The present invention creates an output which can be used as a culling mechanism to reduce the number of objects for human inspection, as a sorting system by numerical threshold, as a search system for features in a visual data set, for off-site human inspection or with a pattern recognition and analysis system for further automated processing. Other applications of the invention as defined in the appended claims will be apparent to persons of skill in the art.

We claim:

1. An apparatus for the inspection of objects in an inspection field for the presence of a target comprising:
   a light source;
   first and second optic sensor means each directed towards said object for concurrent viewing of said object;
   first processor means associated with said first optic sensor for detecting a target and for generating location data for a target;
   said second optic sensor means for selectively acquiring high resolution image data of a located target;
   positioning means for saccadic emulation associated with the second optic sensor means for directing the image data from a target location to the sensor whereby said high resolution target image data is acquired and processed generally immediately following said generation of target location data by said optic sensor and said first processor means; and
   second processor means associated with said second optic sensor for generating an output from the target image data for analysis.

2. An apparatus for the inspection of objects as defined in claim 1, wherein the positioning means associated with the optic sensor means comprises a post-objective scanner.

3. An apparatus for the inspection of objects as defined in claim 2, wherein the post-objective scanner is selectively directable in two axes toward a location on a plane in the inspection field.

4. An apparatus for the inspection of objects as defined in claim 3, wherein the post-objective scanner is directable sequentially towards each target location.

5. Apparatus for the inspection of objects as defined in claim 4, wherein the post-objective scanner has a random access of less than 33 milliseconds.

6. Apparatus for the inspection of objects as defined in claim 5, wherein the scanner has a random access of about 3 milliseconds.

7. An apparatus for the inspection of objects as defined in claim 1, wherein a wide angle optic sensor means is provided to acquire image data of the object to provide to the first processor means for detecting any target and for generating location data for each target.

8. An apparatus for the inspection of objects as defined in claim 7, wherein the wide angle optic sensor means captures low resolution image data of the object, and the optic sensor means comprises a high resolution optic sensor means having a smaller field of view than that of the wide angle sensor means.

9. An apparatus for the inspection of objects as defined in claim 7, wherein the wide angle sensor means and the high resolution sensor means are charge coupled device video cameras.

10. An apparatus for the inspection of objects as defined in claim 7, wherein targets comprise visual anomalies.

11. An apparatus for the inspection of objects as defined in claim 10, wherein the first processor means includes a blob analysis routine for detecting visual anomalies.

12. Apparatus for the inspection of objects as defined in claim 7, wherein the wide angle optic sensor means and the high resolution optic sensor means comprise the same apparatus operating in different modes.

13. Apparatus for the inspection of objects as defined in claim 7, wherein the field of view of the high resolution optic sensor means is variable in response to the target size.

14. An apparatus for the inspection of objects as defined in claim 1, wherein the high resolution image includes a target substantially in the absence of unnecessary data.

15. Use of the apparatus for the inspection of objects as defined in claim 1 for the detection of defects including parasites in fish fillets.

16. A method for the inspection of objects for the presence of targets comprising the steps of:
   providing an apparatus as defined in claim 1;
   detecting any targets on the object with said first optic sensor means;
   generating location data for a detected target;
   emulating saccadic movement to selectively capture a high resolution image of a target with said second sensor means generally immediately following said step of generating location data and without moving said object; and
   generating an output for analysis.

17. A method for the inspection of objects as defined in claim 16, wherein saccadic movement emulation is synchronized to sequentially capture a high resolution image of each target detected at the frame rate of a video imaging means.

18. A method as defined in claim 16, wherein the method includes a first step of treating an object with a marker prior to inspection to identify any targets and a detection means is provided for cooperation with the selected marker for detecting the presence of a target.

19. A method for the inspection of objects as defined in claim 16, wherein the method includes a first step of capturing a first image of at least a portion of an object from which any targets can be detected.

20. A method for the inspection of objects as defined in claim 19, including identifying visual anomalies as targets for detection.

21. A method as defined in claim 16, wherein said object comprises a fish fillet, and said targets include parasites, said step of generating an output for analysis includes the step of processing target image data to determine whether said target is a defect or a parasite and identifying a filet as having a defect or parasite.

22. In an apparatus for the inspection of objects for the presence of targets including an optic sensor, the improvement comprising:
   positioning means for saccadic emulation associated with the optic sensor for directing image data of a target to the sensor including a post-objective scanner.

23. An apparatus for the inspection of objects as defined in claim 22, wherein the post-objective scanner is selectively directable in two axes toward any location on a plane in an inspection field.

24. Apparatus for the inspection of objects as defined in claim 23, wherein the post-objective scanner has a random access of less than 33 milliseconds.

25. Apparatus for the inspection of objects as defined in claim 24, wherein the scanner has a random access of about 3 milliseconds.

26. Apparatus for the inspection of objects as defined in claim 24, wherein the optic sensor comprises a charge coupled device video camera and the scanner has a random access rate which can be synchronized with the frame rate of the camera.

27. Apparatus for the inspection of objects as defined in claim 22, further including a processor means including a blob analysis routine.

28. An apparatus for the inspection of objects for visual targets comprising:

a light source;

a first video imaging means for acquiring a visual image having a field of view including at least a portion of an object and for transmitting image data to a central processor;

a second video imaging means for viewing said object concurrently with said first video imaging means for acquiring a second visual image having a field of view smaller than the field of view of the first video imaging means and for transmitting image data to a central processor immediately following transmission of data from said first video imaging means;

a central processor for receiving image data from the first and second video imaging means and for generating an output for analysis including:

a frame grabber for converting the image data of first and second video imaging means to digital data and isolating a single image;

a digital signal processor assembly programmed for morphological manipulation of the image data from the first video imaging means to detect individual visual anomalies as targets and for generating location coordinates for each target; and a post-objective scanner associated with the second video imaging means including:

a mirror directable in two axes for selectively directing image data from a specified target location to the second video imaging means, and a driver for accessing location coordinates and directing the mirror towards a target location.

29. Apparatus for the inspection of objects as defined in claim 28, wherein the video imaging means comprise charge coupled device video cameras and the scanner has a random access rate which can be synchronized with the frame rate of the camera.

30. An automated station for the detection of defects including parasites in fish fillets including:

a viewing head comprising:

first image recording means for viewing said object concurrently with said first image recording means and for acquiring image data of an object in an inspection field;

second image recording means having a smaller field of view than that of the first image recording means for selectively acquiring higher resolution image data;

positioning means associated with the second image recording means, for directing image data of substantially only a target to the second image recording means including a post-objective scanner directable in two axes toward any location on a plane in the inspection field;

a candling table for back-lighting a fillet;

a light source for providing illumination of the inspection field;

advancing means for presenting a fillet on the candling table to the first and second cameras;

a support for supporting the viewing head a distance from the candling table;

first processor means for processing the image data of the object to isolate any targets, and for generating location data for each target;

second processor means for generating an output from the target image data for analysis; and wherein said first and second image recording means, and said first and second processor means operate generally one immediately following the other to emulate the functioning of a human eye to generally nearly simultaneously or in rapid succession identify targets within a broad field of view and resolve such targets within a narrow field of view at higher resolution.

* * * * *

UNITED STATES PATENT AND TRADEMARK OFFICE
CERTIFICATE OF CORRECTION

PATENT NO. : 6,061,086
DATED : May 9, 2000
INVENTOR(S) : Ernest M. Reimer, Paul Hearn, Ivi Hermanto Page 1 of 1

It is certified that error appears in the above-identified patent and that said Letters Patent is hereby corrected as shown below:

<u>Title page,</u>
Item [73] Assignee should read as follows:

-- [73] Assignee: Canpolar East Inc. --

Signed and Sealed this

Fourth Day of September, 2001

*Attest:*

NICHOLAS P. GODICI
*Attesting Officer*    *Acting Director of the United States Patent and Trademark Office*